United States Patent
Rehberger et al.

(10) Patent No.: US 8,021,655 B2
(45) Date of Patent: *Sep. 20, 2011

(54) METHODS OF FEEDING RUMINANTS

(75) Inventors: Thomas G. Rehberger, Wauwatosa, WI (US); John P. O'Neill, West Allis, WI (US)

(73) Assignee: Board of Regents for Oklahoma State University, Stillwater, OK (US)

( * ) Notice: Subject to any disclaimer, the term of this patent is extended or adjusted under 35 U.S.C. 154(b) by 343 days.

This patent is subject to a terminal disclaimer.

(21) Appl. No.: 12/276,007

(22) Filed: Nov. 21, 2008

(65) Prior Publication Data

US 2009/0136622 A1      May 28, 2009

Related U.S. Application Data

(60) Continuation of application No. 10/980,878, filed on Nov. 3, 2004, now Pat. No. 7,470,531, which is a division of application No. 09/912,049, filed on Jul. 24, 2001, now Pat. No. 6,951,643.

(51) Int. Cl.
 *A01N 63/00* (2006.01)
(52) U.S. Cl. ........................ 424/93.4; 435/252.1; 426/61
(58) Field of Classification Search ........................ None
 See application file for complete search history.

(56) References Cited

U.S. PATENT DOCUMENTS 6,951,643 B2 * 10/2005 Rehberger et al. ........... 424/93.4

OTHER PUBLICATIONS

Kim, S.W. et al. "Potential Use of Propionibacterium acidipropionici, strain DH42 as a direct-fed microbial for cattle", Michigan State University—Beef Cattle, Sheep and Forage Systems Research and Demonstration Report, 2001.
Office Action mailed Nov. 17, 2009 for Canadian App. No. 2,455,399.

* cited by examiner

*Primary Examiner* — Irene Marx
(74) *Attorney, Agent, or Firm* — Whyte Hirschboeck Dudek S.C.

(57) ABSTRACT

An isolated microorganism comprising a Propionibacteria strain is described. When the microorganism is fed to a ruminant, protein and fat levels in milk produced by the ruminant are increased, while body condition and milk production levels are maintained. When fed to the ruminant, the microorganism also has positive effects on various metabolic hormones and metabolites, e.g, an increase in energy balance, plasma non-esterified fatty acids levels, and plasma leptin level. Supplementation with propionibacteria reduced dry matter intake but did not affect milk production in the cows. Therefore, the propionibacteria of the invention made the cows more energy efficient as cows produced the same amount of milk, yet consumed less dry matter.

11 Claims, 10 Drawing Sheets

METHODS OF FEEDING RUMINANTS

CROSS-REFERENCE TO RELATED APPLICATIONS

This application is a continuation of Ser. No. 10/980,878, which is a divisional of U.S. patent application Ser. No. 09/912,049, filed Jul. 24, 2001, now U.S. Pat. No. 6,951,643, the entireties of both of which are incorporated herein by reference.

BIBLIOGRAPHY

Complete bibliographic citations of the references referred to herein by the first author's last name in parentheses can be found in the Bibliography section, immediately preceding the claims.

FIELD OF THE INVENTION

The invention relates to microorganisms for ingesting by animals. More particularly, though not exclusively, the present invention relates to microorganisms that are useful as a direct-fed for ruminants.

DESCRIPTION OF THE RELATED ART

Milk solid components include protein, fat, lactose, and minerals. Milk protein has economic value because, for example, higher protein leads to higher cheese yields. Furthermore, in recent years, consumers have become increasingly concerned about the effects of dietary fat consumption on their health. Low fat milk and low fat cheese have become popular. In many countries, including the United States, the payment for milk shipped to cheese plants has changed to a system based on both protein and fat content from one based on milk fat. This market trend increases the emphasis on milk protein. However, milk fat continues to be an important component in some markets were it is used to make ice cream and butter. In these markets, a premium of $2 per pound is paid for milk fat.

Milk protein represents about 3% to about 4% of the total content of milk, depending on numerous factors, including animal breed and diet. Milk protein is synthesized in the mammary gland from amino acids. The biological control mechanism of milk protein synthesis is still largely unknown. Milk protein requires a supply of the appropriate amino acids as well as a source of energy at the mammary gland.

Ruminal volatile fatty acids affect the concentration of fat and protein in milk. In general, increasing propionate production increases the concentration of protein in milk, while increasing acetate increases the concentration of fat in milk.

The volatile fatty acids are the major precursors of glucose, which is used to create energy for the physiological processes in the animal. Dairy cattle fed typical diets high in starch produce volatile fatty acids in the following proportions: 58% acetate, 30% propionate, and 12% butyrate. Propionate production conserves 109% of the energy from glucose, while acetate production conserves only 77%.

Energy balance is the difference between the amount of energy consumed by an animal and the amount of energy expended by the animal. The energy balance of an animal can be in a positive or negative state, and it can be measured. The effect of dietary protein and energy supply on milk protein synthesis is affected by rumen fermentation. Dietary proteins are broken down to their constituent amino acids during digestion. The amino acids are absorbed into the body. Carbohydrates in the diet are degraded by the rumen microorganisms to volatile fatty acids, which are the major energy supply for the cow.

Many high producing dairy cows are unable to consume enough feed to meet energy demands during early postpartum lactation, resulting in a state of negative energy balance. Energy balance (EB) is quantified using measures of dry matter intake (DMI), milk production (quantity and composition), and body weight (BW) and may be associated with reproductive efficiency. In lactating dairy cows, EB during the first few weeks postpartum is positively related to concentrations of plasma progesterone ($P_4$) during the first postpartum estrous cycle (Berghorn et al., 1988; Villa-Godoy et al., 1988; Spicer et al., 1990). Cows exhibiting estrus with subsequent formation of a functional corpus luteum that secretes maximal $P_4$ levels have the best chance of maintaining pregnancy (Villa-Godoy et al., 1988). In addition, cows that express estrus before first postpartum ovulation have greater EB than cows that do not express estrus (Berghorn et al., 1988; Spicer et al., 1990). Negative EB is therefore a likely cause for poor reproductive efficiency in lactating dairy cows (Kimura et al, 1987; Sklan et al., 1991).

Although studies implicate EB as a regulator of ovarian function, the hormones or metabolites mediating the effect of EB are unclear. Plasma cholesterol (Carroll et al., 1990) and insulin (Koprowski and Tucker; 1973; Smith et al., 1978) increase whereas plasma non-esterified fatty acids (NEFA) decrease (Staples and Thatcher, 1990; Canfield and Butler, 1991; Beam and Butler, 1998) with increasing week of lactation. Concentrations of cholesterol in blood of cattle are modified by variations in fat, protein and (or) energy intake and increase as EB increases (Kronfeld et al., 1980; Grummer and Carroll 1988; Ronge et al., 1988; Spicer et al., 1990; 1993). Because insulin in vitro stimulates mitogenesis and steroidogenesis of bovine ovarian cells (Schams et al., 1988; McArdle et al., 1989; McArdle et al., 1991; Saumande et al., 1991; Spicer, et al, 1993, Gong et al., 1994; Spicer and Chamberlain, 1998), negative EB may affect ovarian activity by decreasing luteal progesterone ($P_4$) production (Talavera et al., 1985; Grummer and Carroll, 1991; Spicer et al., 1993; Hawkins et al., 1995).

Propionate, a ruminal volatile fatty acid, acts as a precursor for hepatic glucose production. Glucose is used to create energy for the physiological processes in the animal. Drenching the diet of lactating cows with calcium propionate elevates plasma glucose concentration (Jonsson et al., 1998). Conversely, preventing reabsorption of glucose in renal tubules decreases plasma glucose and insulin in dairy cows (Amaral-Phillips et al., 1993). Also, infusion of butyrate, a ruminal volatile fatty acid that inhibits the use of propionate for gluconeogenesis into the rumen of lactating cows, decreases plasma glucose concentrations (Huhtanen et al., 1993). Whether plasma insulin, IGF-I, cholesterol, and other metabolites are altered by changes in ruminal propionate is unknown.

Propionibacteria are natural inhabitants of the rumen that comprise 1.4% of the ruminal microflora and produce propionic and acetic acid in the rumen (Oshio et al., 1987). Directly feeding propionibacteria may increase hepatic glucose production via increased in ruminal propionate production and absorption. The efficiency of utilization for maintenance of metabolizable energy of propionic acid is 0.86 vs. 0.59 for acetate and 0.76 for butyrate (McDonald et al., 1987). Organisms of the genus *Propionibacterium* comprise a small proportion of the ruminal microflora and are slow growing. Propionibacteria are an industrially important group of organisms primarily used by the dairy-food industry as starter cultures for Swiss-type cheeses. Other industrial applications of the propionibacteria have been described including their use in the production of vitamin B12 and propionic acid and as inoculants for silage and grain. Other applications of the propionibacteria include their use as direct-fed microbials. However, little research has been reported to date.

With the adoption of recent economic incentives for producing milk of a desired composition, dairy farmers can realize an economic benefit by feeding specific dietary enhancements to manipulate ruminal fermentation. Therefore, dairy farmers will benefit from products that can successfully control or manage ruminal microbial fermentation activity.

In view of the foregoing, it would be desirable to provide a direct-fed microbial which, when fed to ruminants, increases the protein and fat levels in milk produced by the ruminant while maintaining body condition and milk production levels. It would also be desirable for the microorganism, when fed to livestock, to have a positive effect on various metabolic hormones and metabolites.

SUMMARY OF THE INVENTION

The invention, which is defined by the claims set out at the end of this disclosure, is intended to solve at least some of the problems noted above. Isolated Propionibacteria strains are provided. In a preferred embodiment, the strains are *P. acidipropionici* or *P. jensenii*.

A method of feeding a ruminant the microorganism is also provided. Feeding ruminants the microorganism increases at least one of energy balance, plasma non-esterified fatty acids levels, and plasma leptin level in the ruminant fed the microorganism when compared to the respective energy balance, plasma non-esterified fatty acids levels, and plasma leptin level in the ruminant when not fed the microorganism. Milk from ruminants fed the microorganism has a higher percent of protein than the percent of protein in milk produced by the ruminant when not fed the microorganism. The milk also has a higher fat level when compared to milk produced by the ruminant when not fed the microorganism.

A feed composition is also provided. The feed composition includes the isolated microorganism described above and a carrier.

A method of forming a direct fed is also provided. The method includes steps of growing, in a liquid nutrient broth, a culture including the isolated microorganism described above, and separating the microorganism from the liquid nutrient broth. The separated microorganism can then be freeze-dried and added to a carrier.

BRIEF DESCRIPTION OF THE DRAWINGS

Preferred exemplary embodiments of the invention are illustrated in the accompanying drawings.

Figure 1:
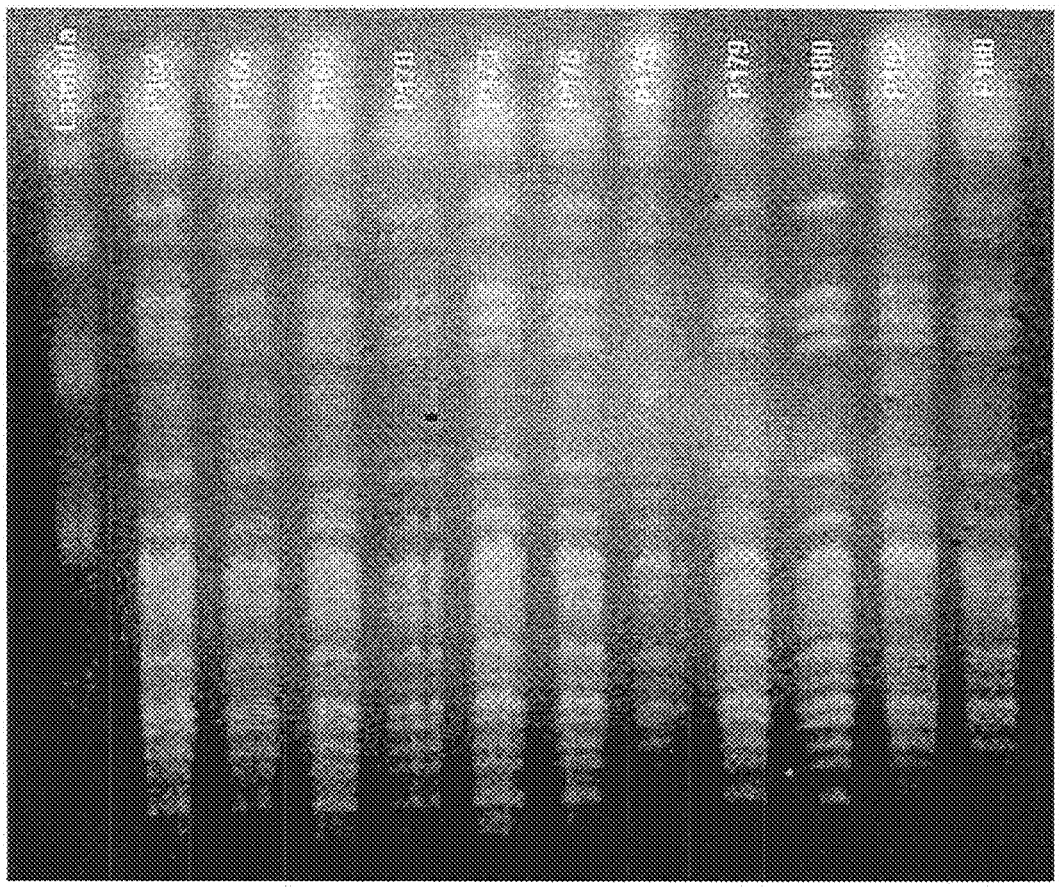
FIGS. 1 and 2 show pulsed-field gel electrophoresis analysis of Xba I digested genomic DNA of *Propionibacterium* strains. Strain identifications are shown.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

In accordance with the present invention, there may be employed conventional molecular biology and microbiology within the skill of the art. Such techniques are explained fully in the literature. See, e.g., Sambrook, Fritsch & Maniatis, Molecular Cloning: A Laboratory Manual, Third Edition (2001) Cold Spring Harbor Laboratory Press, Cold Spring Harbor, N.Y.

Microorganisms:

Propionibacteria strains useful in the invention were selected based on several criteria. One or more of the following criterion were used to select useful propionibacteria strains: 1) production of at least 0.9% propionate (vol/vol) in sodium lactate broth (NLB) and at least 0.2% propionate (vol/vol) in rumen fluid (in vitro), 2) isolation from the rumen, 3) ability to survive and grow in the rumen, 4) ability to be grown commercially, and 5) ability to survive a freeze-drying process. All of the strains possessing one or more of these properties had a genetic profile of group 1 (as defined below). Strains possessing one or more of these properties were then tested in vivo. When fed to ruminants, the tested strain increased protein and fat levels in milk produced by the ruminants, while maintaining body condition and milk production levels. When fed to ruminants, the tested strain increased plasma leptin levels and decreased dry matter intake, making the lactating cows more energetically efficient.

Preferably, the microorganisms of the invention are selected from the genus *Propionibacterium*. The microorganisms were isolated from the rumen of fistulated ruminants. Multiple collections of rumen fluid were obtained over a period of time. Colonies were isolated. The colonies that were suspected of being Propionibacteria were then grown in broth, and the strain of the isolates was determined based on biochemical tests and carbohydrate fermentation patterns. Based on carbohydrate fermentation patterns and biochemical tests, 95% of the isolates were identified as *P. acidipropionici* and the remaining 5% were identified as *P. jensenii*.

The plasmid contained within each isolate was examined to determine whether plasmids carried by the isolates had an effect on survival and function in ruminant environments. Overall, 35% of the 132 isolates examined contained plasmids. Two plasmid profiles were common, a single 2.5 kb plasmid and a single 7.0 kb plasmid. Only one strain was found to contain more than one plasmid. The predominant plasmid profile varied at different sampling times.

The intact genomic DNA from the isolates was also examined to determine the genetic diversity of the strains and to reduce the number of strains subsequently tested in feeding experiments. Pulsed-field gel electrophoresis analysis of genomic DNA identified 13 distinct Xba I fragment patterns. However, only one strain was predominant in the rumen of all cows throughout the sampling times.

The isolates were then tested for volatile fatty acid production. Various fatty acids such as propionate, acetate, butyrate, and lactate were detected and concentration determined. An isolate that produced the highest amount of propionate under conditions similar to the rumen was selected for animal testing.

In a preferred embodiment, the microorganism is of the genus *Propionibacterium* and more preferably *P. acidipropionici* and *P. jensenii*. Preferred strains of bacteria include *P. acidipropionici* and *jensenii* strains P169, P170, P179, P195, and P261, especially strain, P169. The P169 and P170 strains are available from the microorganism collection of the American Type Culture Collection (ATCC), 10801 University Blvd., Manassas, Va. 20110, under accession numbers ATCC PTA-5271 and ATCC PTA-5272, respectively, and were deposited on Jun. 18, 2003. Strains P179, P195, and P261 were deposited on Apr. 2, 2008 at the Agricultural Research Service Culture Collection (NRRL), 1815 North University Street, Peoria, Ill., 61604 and given accession numbers NRRL B-50133, NRRL B-50132, and NRRL B-50131, respectively. All of the preferred strains were found to have group 1 genomic profiles (as defined below). Therefore, other strains of *P. acidipropionici* or *P. jensenii* that have a group 1 genomic profile and which have a common identifying characteristic of successful performance in the present invention are also preferred strains. These other strains are referred to hereinafter as "genetic equivalents."

Direct Feed Assays on Cows:

Strain P169 was used in animal trials to determine the effects of the direct-fed propionibacteria on energy balance, milk yield and composition, metabolites and hormones of early lactating dairy cows.

In a first study in which cows were fed freeze-dried propionibacteria culture, in the control group, there was a decline in rumen pH during the 11.5 h after the morning allocation of concentrate (−0.486 pH units). In contrast, in the cows that received the *Propionibacterium*, the decline in rumen pH occurred during 6 h after the morning feed (−0.32 pH units) and then remained relatively stable before returning to a pre-feeding value. Thus, the *Propionibacterium* had a physiological effect on the cows.

In a second animal study, nineteen pluriparous Holstein cows were individually fed a total mixed ration from −2 to 12 wk postpartum. Each treated cow received 17 g of a 1:10 preparation of the freeze-dried propionibacteria culture, which was at a concentration of about $3.5 \times 10^{10}$ CFU/g, and maltodextrin carrier daily. Daily feed intake and milk production and weekly body weight were recorded. Blood samples were collected twice a week for quantifications of plasma cholesterol, non-esterified fatty acids (NEFA), leptin, insulin, and glucose. When compared to control cows, cows supplemented with Propionibacteria culture improved energy balance (EB) and body weight at the first week of lactation. Supplementation with propionibacteria reduced dry matter intake (DMI) when expressed as g DMI per kg body weight, but did not affect milk production in the cows. Therefore, the propionibacteria made the cows more energy efficient as cows produced the same amount of milk, yet consumed less dry matter. When compared to control cows, cows fed Propionibacteria had greater percentages of milk protein and solids-non-fat (SNF) during the first week of lactation and in addition, the percentages of milk fat increased over the 12 weeks of observation. Thus, due to economic incentives for milk fat, feeding cows propionibacteria of the invention provides economic advantages to dairy farmers. Plasma glucose, insulin, and cholesterol concentrations were not significantly affected by supplemental feeding of Propionibacteria culture. Thus, there was no negative effect on these parameters.

Plasma NEFA concentrations at week 1 of lactation was significantly lower in control than treated cows but not thereafter. Decreasing plasma NEFA concentrations with week postpartum may be an indication that the cows are moving towards positive EB.

Manipulation of the ruminal fermentation to increase propionate improves the energetic efficiency of the animal. As energy efficiency is increased, a positive energy balance is obtained, which has a direct effect on reproductive efficiency. Cows with a positive energy balance have a greater chance of maintaining pregnancy, which is necessary to effectively increase milk production over the life of the cow.

Leptin, which is a neurotransmitter produced by fat cells and involved in the regulation of appetite, was significantly higher in treated cows than control cows throughout the study. Leptin from adipocytes passes from circulation to the cerebrospinal fluid and to the hypothalamus and may affect satiety. Thus, the direct fed had positive effect on cows' plasma leptin levels, which may be an important signal for regulation of feed consumption that indirectly influences milk production, energy status, and reproductive functions.

In sum, feeding Propionibacteria culture strain P169 to early lactating dairy cows improved some production parameters of lactation but without negatively impacting reproductive function.

Preparation and Feeding of Direct-Fed Propionibacteria:

In a preferred embodiment, the microorganism is fed to a ruminant, and the microorganism becomes established in the rumen. Preferably, the amount of the microorganism that is delivered to the ruminant is about $6 \times 10^{9}$ CFU to about $6 \times 10^{12}$ CFU/animal/day. This translates into approximately $1 \times 10^{5}$ to $1 \times 10^{8}$ CFU/ml of rumen fluid for an averaged sized cow. In a more preferred embodiment, about $6 \times 10^{11}$ CFU/animal/day of the microorganism is delivered to the ruminant. In a preferred embodiment, the microorganism is fed to a ruminant such that the microorganism becomes established in the rumen at a level of about $1 \times 10^5$ CFU per ml of ruminen fluid to about $1 \times 10^8$ CFU per ml of ruminen fluid.

The microorganism of the present invention may be presented in various physical forms, for example as a top dress, liquid drench, gelatin capsule, or gels. In a preferred embodiment of the top dress form of the microorganism, freeze-dried *Propionibacterium* fermentation product is added to a carrier, such as whey, maltodextrin, sucrose, dextrose, limestone (calcium carbonate), rice hulls, yeast culture, dried starch, sodium silico aluminate. In a preferred embodiment of the liquid drench, freeze-dried *Propionibacterium* fermentation product is added to a carrier, such as whey, maltodextrin, sucrose, dextrose, dried starch, sodium silico aluminate, and a liquid is added to form the drench. In a preferred embodiment of the gelatin capsule form, freeze-dried *Propionibacterium* fermentation product is added to a carrier, such as whey, maltodextrin, sugar, limestone (calcium carbonate), rice hulls, yeast culture dried starch, sodium silico aluminate. The Propionibacteria and carrier are enclosed in a rumen degradable gelatin capsule. In a preferred embodiment of the gels form, freeze-dried *Propionibacterium* fermentation product is added to a carrier, such as vegetable oil, sucrose, silicon dioxide, polysorbate 80, propylene glycol, butylated hydroxyanisole, citric acid, and artificial coloring to form the gel.

In one preferred embodiment of the present invention, a microorganism is directly fed to a ruminant to increase the protein and fat concentration in milk produced by animals fed the microorganisms and to have a positive effect on various metabolic hormones and metabolites.

In a preferred embodiment, the *P. acidipropionici* is fermented to a $5 \times 10^8$ CFU/ml to a $4 \times 10^9$ CFU/ml level with a level of $2 \times 10^9$ CFU/ml being more preferred. The bacteria are harvested by centrifugation, and the supernatant is removed. The pelleted microorganisms can then be fed to the ruminant. Preferably, the pelleted microorganisms are freeze-dried for direct feeding to the ruminant.

In a preferred embodiment, the microorganisms are added to animal feed. Preferably, the microorganism is fed as mixture of freeze-dried microorganism, which is at a concentration of about $3.5 \times 10^{10}$ CFU/g and a carrier, which preferably is a maltodextrin carrier. Preferably, about 17 g of the 1:10 mixture is fed to each animal each day. In a preferred embodiment, the microorganism is fed from 2 weeks prior to parturition to 12 weeks postpartum, although the microorganism can be fed for different durations and at different times.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Isolation of Propionibacteria

The propionibacteria strains examined in this study were obtained from rumen fluid collected from five fistulated Holstein cows at the Oklahoma State University Dairy Cattle Research Center. Rumen fluid was collected three times over a five month period, spanning 150 days of the 305 day lactation. The cows received a ration concurrent with the pounds of milk produced daily (See Table 1).

TABLE 1

| Ration Content | | |
|---|---|---|
| Ration Mix | % as fed Pen A | % as fed Pen B |
| Alfalfa | 7.8 | 2.2 |
| Sorghum | 44.6 | 66.4 |
| Whole corn | 7.5 | 2.1 |
| Grain mix | 38.0 | 27.1 |
| Shelled corn (67%) | | |
| Soybean meal (27%) | | |
| Molasses (3%) | | |
| Limestone (1%) | | |
| Dicalcium phosphate (1%) | | |
| Trace minerals (1%) | | |
| Prairie hay | 2.1 | 2.2 |
| Bypass protein | 1 lb | |

** Cow 179 fed Pen A Ration, all others Pen B ration.

At each sampling time approximately 100-150 ml rumen fluid was collected from beneath the mat of ingesta or squeezed from the ingesta into 250 ml bottles. The fluid was transported to the laboratory and strained through cheesecloth to remove the feedstuff debris. The fluid was then diluted and plated onto a selective agar containing erythritol as the carbon source with the pH indicator bromocresol purple with selective antibiotics. All plates were incubated for 7-10 days at 32° C. under anaerobic conditions ($CO_2$ GasPak®, B-D Laboratories, Inc. East Rutherford, N.J.). After 7-10 days, the plates were examined for smooth, raised, convex colonies, which fermented erythritol as indicated by a pH change in the agar medium. Propionibacteria colonies were yellow due to the bromocresol purple indicator changing from purple to yellow as the erythritol was fermented and acid was formed. Individual colonies were picked from the original serial dilution plates of rumen fluid and streaked on four consecutive streak plates to ensure purity.

Isolated colonies were picked into 10 ml tubes of sodium lactate broth (NLB) and incubated statically for 36-48 hours at 32° C. The cultures were routinely propagated from 1% transfers in NLB. Cultures can be stored as frozen stocks at −75° C. in, for example, NLB with 10.0% glycerol.

Identification of Propionibacteria Isolates:

Colonies suspected of being propionibacteria colonies were grown in 10 ml NLB tubes for 36 hours at 32° C. After incubation, the isolates were gram stained and tested for catalase production. Gram positive, pleomorphic rods with characteristic V or Y configurations were tested for their ability to ferment lactose, mannitol, and trehalose. Further identification was made by observing the reduction of esculin (0.01%) and nitrate (0.2%) as well as the hydrolysis of gelatin (12%). Gram positive isolates that reduced esculin and nitrate were classified as *P. acidipropionici* and non-nitrate reducing Gram positive, esculin reducers were classified as *P. jensenii*. It should be noted that the biochemical tests used to distinguish *P. acidipropionici* from *P. jensenii* is not 100% conclusive. For example, occasionally, when tests are repeated, the species classification changes. The genomic DNA grouping described below is a more accurate classification method.

The isolates were tested for volatile fatty acid production using a Hewlett-Packard® 1090 HPLC. The isolates were grown from a 1% transfer in 10 ml NLB incubated for 36 hours at 32° C. The cells were removed from the media by centrifugation (1500×g 15 min) and the supernatant was then filtered through 0.2 um Gelman® filter and mixed with equal volumes of 0.01 M $H_2SO_4$. 1 ml samples were injected (5 ul) and separated using a HPX-87H column (BioRad®) preheated to 65° C. with 0.005 M $H_2SO_4$ as the mobile phase at a flow rate of 1 ml/min. Propionate, acetate, butyrate, and lactate were detected using a diode array detector scanning wavelengths 210-254 nm. Concentrations were determined by calculating peak areas and comparing these to known areas of external standards using Hewlett-Packard® software.

A total of 132 strains isolated from the rumen fluid were identified as *Propionibacterium* based on a gram-positive, pleomorphic cell morphology, the reduction of esculin, hydrolysis of gelatin, and production of propionate and acetate from lactate. All isolates examined in this study fermented mannitol and trehalose. All but three of the isolates fermented lactose. A total of 126 strains reduced nitrate and 26 of these isolates were found to reduce nitrite as well. Based on these results, 126 of the isolates were identified as *P. acidipropionici* (capable of nitrate reduction), and the remaining five were identified as *P. jensenii*. It should be noted that the tests used to distinguish *P. acidipropionici* from *P. jensenii* is not one hundred percent conclusive. Occasionally, when tests are repeated, the species classification changes. The genomic DNA grouping described below is a more accurate classification method.

Ruminal populations of propionibacteria ranged from $10^3$ to $10^4$ CFU/ml. Propionibacteria populations varied among different cows at different sampling times. Three of the five cows used in this study had detectable propionibacteria populations at two of the sampling times while one cow had detectable propionibacteria populations at all three sampling times. Only one cow did not have detectable populations of propionibacteria at any of the sampling times. Isolates characterized as *P. acidipropionici* were predominant at all sampling times and accounted for 96% of the total propionibacteria isolated from the rumen.

Strains P169, P170, P179, P195, and P261 produced at least 0.9% (vol/vol) propionate in sodium lactate broth (NLB) and at least 0.2% (vol/vol) propionate in rumen fluid (in vitro).

Plasmid DNA Isolation:

In an effort to determine whether plasmids carried by the isolates had an effect on survival and function in ruminant environments, plasmid DNA was isolated from the propionibacteria strains and DNA analysis was performed. The DNA was resuspended in 40 ul Tris-EDTA buffer and 5 ul tracking dye and then loaded onto an agarose gel. The DNA was separated by gel electrophoresis using a 0.7% agarose gel at 50 volts. The agarose gels were then examined after 45 minutes of staining in ethidium bromide solution.

Referring to Table 2 below, plasmids were detected in 32.6% (43 out of 132) of the isolates screened. Only one strain contained more than one plasmid. Of the 42 isolates that contained a single plasmid, 31 strains contained a 2.7 kb plasmid and the remaining 11 strains contained a 7.0 kb plasmid. There was no apparent relationship between plasmid content and the biochemical and fermentation activity of the isolates. In addition, it is not known whether plasmids of the same molecular weight found in different isolates are in fact identical.

TABLE 2

Plasmid DNA analysis of propionibacteria isolates.

| Sampling Date | Number of Isolates Screened | Plasmid Content | | |
|---|---|---|---|---|
| | | Number of Isolates | Number of Plasmids | MW (kb) |
| February | 31 | 20 | 0 | all 7.0 |
| | | 11 | 1 | |
| April | 35 | 31 | 1 | all 2.7 |

TABLE 2-continued

Plasmid DNA analysis of propionibacteria isolates.

| Sampling Date | Number of Isolates Screened | Plasmid Content | | |
|---|---|---|---|---|
| | | Number of Isolates | Number of Plasmids | MW (kb) |
| | | 4 | 0 | |
| June | 66 | 65 | 0 | 1.6, 1.8 |
| | | 1 | 2 | |

The predominant plasmid profile was different at each sampling time (Table 2). Plasmids of similar molecular weight were not detected at different sampling times. The absence of plasmids in the majority of strains (67.4%) and the lack of conserved plasmids among isolates at different sampling times may indicate the plasmids detected are not important for survival and function in the ruminal environment.

Preparation of Intact Genomic DNA:

In an effort to determine the genetic diversity of the strains and to reduce the number of strains subsequently tested in direct feed experiments, intact genomic DNA from representative strains was isolated from cells embedded in agarose beads. Cultures were grown to mid-log stage in 10 ml NLB with supplemented varying percentages of glycine. The cells were harvested by centrifugation (9000×g for 10 min) and resuspended to one-tenth the original volume in 10×ET buffer (*500 mM EDTA, 10 mM Tris-HCl, pH 8.0). The cell suspension was mixed with an equal volume of 1% low-melting point agarose (Beckman Instruments, Palo Alto, Calif.), loaded into a syringe, and injected into Tygon® tubing (ID-1/16", OD-1/8") where it was allowed to solidify. The solidified cell-agarose mixture was forced through the tubing into cold 10×ET buffer and chopped into smaller pieces (beads). The beads were harvested (5500×g for 10 min), resuspended in 10 ml 10×ET containing 5 mg/ml lysozyme and incubated at 32° C. with gentle shaking for 2 hours. After incubation, the beads were harvested by centrifugation (5500×g for 10 min) and resuspended in 10 ml of lysis buffer (10×ET buffer containing 100 ug/ml of Proteinase K and 1% Sarkosyl®), and incubated at 55° C. for 15 hours to lyse cells and release the genomic DNA. After lysis, the beads were harvested by centrifugation (5500×g for 10 min), resuspended in 10 ml of 1 mM phenylmethylsulfonyl fluoride, and incubated at room temperature for 2 hours with gentle shaking to remove contaminating protease activity. The beads of purified DNA were washed three times in TE buffer (10 mM Tris-HCl, 1 mM EDTA-Na$_2$, pH 7.5), resuspended in 10 ml TE buffer, and stored at 4° C. until restriction endonuclease digestion was performed.

In Situ Restriction Endonuclease Digestion and Pulsed-Field Gel Electrophoresis of Genomic DNA:

Agarose beads containing DNA were equilibrated in 1× restriction endonuclease buffer for 1 hour before enzyme digestion. After equilibration, 10-20 units of the restriction enzyme were added to 90 ul of beads and incubated at the appropriate temperature for 6-8 hours. Following digestion, the enzymes were inactivated by heating for 5 minutes at 65° C. The melted beads were loaded onto a gel for fragment separation.

DNA fragments were separated on 1.0% agarose gels in 0.5×TBE buffer at 15° C. for 23 hours using a CHEF-DRIII electrophoresis system (BioRad®). Each set of restriction endonuclease digests were separated at different initial and final pulse times to provide maximum separation of small, medium, and large fragments. To determine the molecular size of the DNA fragments lambda DNA multimers, intact yeast chromosomes and restriction fragments of lambda DNA were included as standards.

Figure 2:
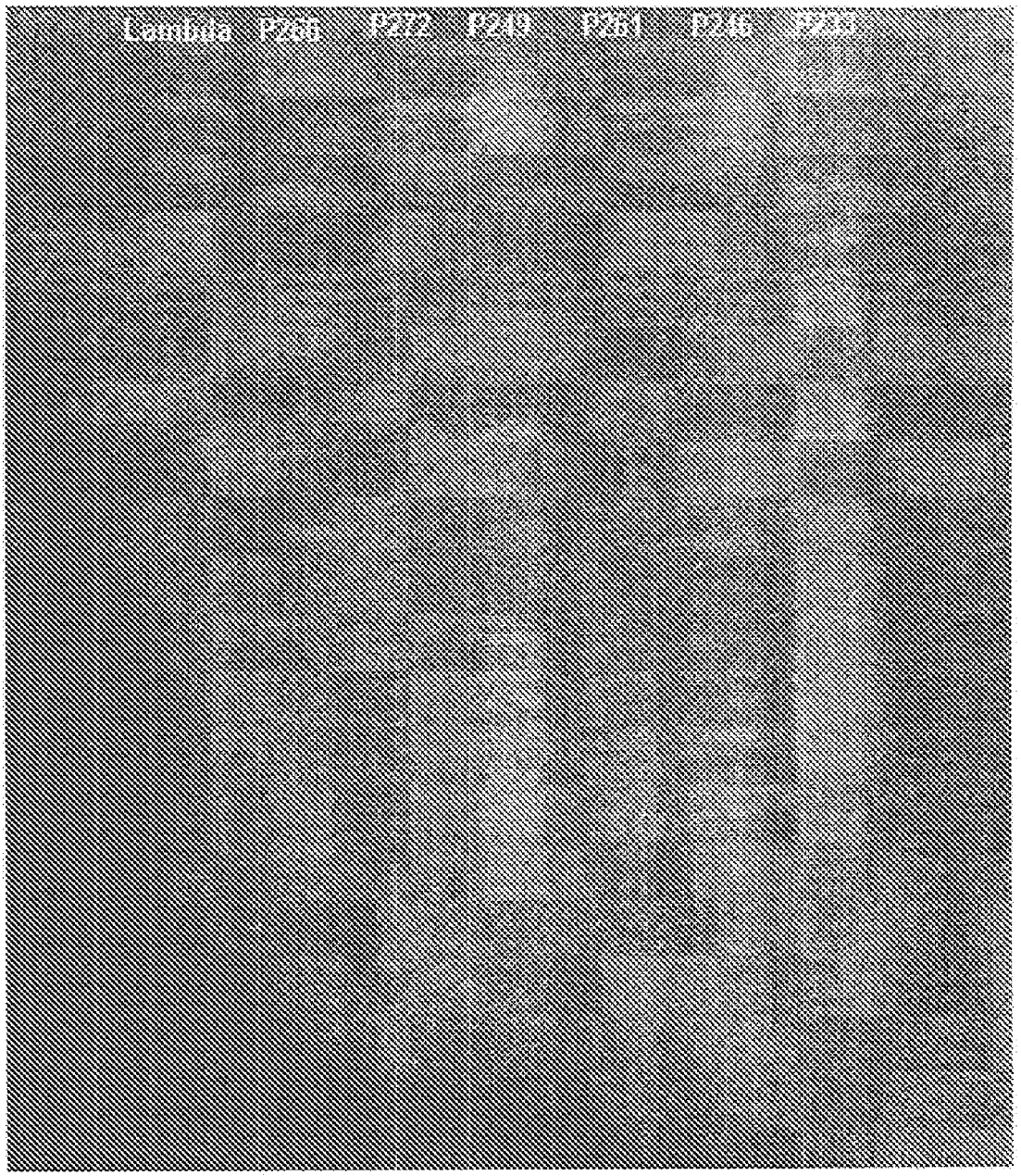

Comparisons of genomic DNA profiles produced by Xba I digests identified isolates that shared the same DNA digestion pattern (FIGS. 1 and 2). Isolates with a common digestion pattern (>90% of the fragments comigrating) were assigned to the same genomic digestion profile group, which are shown below in Table 3. Overall, 21 different digestion profiles were observed for the 132 isolates. Eight of the profiles were unique to only one isolate. The predominant genomic profile (group 1) was shared by 48 isolates, which accounted for 43.6% of all isolates examined.

TABLE 3

Analysis of propionibacteria isolates.

| Isolate Number | Species Identification | Plasmid Content | | Genomic digestion profile group |
|---|---|---|---|---|
| | | Number of Plasmids | MW (kb) | |
| 162 | P. acidipropionici | 0 | | 1 |
| 166 | P. acidipropionici | 0 | | 1 |
| 169 | P._acidipropionici | 0 | | 1 |
| 170 | P. acidipropionici | 0 | | 1 |
| 173 | P. acidipropionici | 0 | | 1 |
| 176 | P. acidipropionici | 0 | | 1 |
| 178 | P. acidipropionici | 0 | | 1 |
| 179 | P. jensenii | 0 | | 1 |
| 180 | P. acidipropionici | 0 | | 1 |
| 182 | P. acidipropionici | ND | | 1 |
| 188 | P. acidipropionici | 0 | | 1 |
| 195 | P. jensenii | 1 | 7.0 | 2 |
| 233 | P. acidipropionici | 0 | | 3 |
| 236 | P. acidipropionici | 1 | 2.7 | 4 |
| 238 | P. acidipropionici | 1 | 2.7 | 1 |
| 245 | P. acidipropionici | 1 | 2.7 | 1 |
| 246 | P. acidipropionici | 1 | 2.7 | 1 |
| 248 | P. acidipropionici | 1 | 2.7 | 1 |
| 249 | P. acidipropionici | 1 | 2.7 | 1 |
| 261 | P. acidipropionici | 1 | 2.7 | 1 |
| 266 | P. acidipropionici | 0 | | 3 |
| 272 | P. acidipropionici | 1 | 2.7 | 1 |
| 277 | P. acidipropionici | 0 | | 3 |
| 279 | P. acidipropionici | 1 | 2.7 | 1 |
| 345 | P. acidipropionici | 0 | | 6 |
| 346 | P. acidipropionici | 0 | | 10 |
| 347 | P. acidipropionici | 0 | | 10 |
| 348 | P. acidipropionici | 0 | | 6 |
| 349 | P. acidipropionici | 0 | | 6 |
| 350 | P. acidipropionici | 0 | | 5 |
| 351 | P. acidipropionici | 0 | | 6 |
| 352 | P. acidipropionici | 0 | | 6 |
| 354 | P. acidipropionici | 0 | | 5 |
| 362 | P. acidipropionici | 0 | | U |
| 365 | P. acidipropionici | 0 | | U |
| 377 | P. acidipropionici | 0 | | U |
| 381 | P. acidipropionici | 0 | | U |
| 388 | P. acidipropionici | 0 | | U |
| 393 | P. acidipropionici | 0 | | 5 |
| 395 | P. acidipropionici | 0 | | U |
| 400 | P. acidipropionici | 0 | | U |

ND = Not determined
U = Unique genomic profile

Little diversity of the genomic digestion patterns was observed in isolates from the first two sampling periods. The group 1 digestion profile was observed for 77.4% of the isolates obtained in the first two sampling periods. However, this digestion profile failed to be detected in isolates from the June sampling. Other changes in the genomic profiles of isolates from the June sampling were also detected. None of the genomic profiles observed in isolates from the first two sampling times were observed in the isolates obtained in the June sampling. In addition, the diversity of the genomic profiles increased from 2 and 3 profiles detected in the first and second sampling periods, respectively (a total of 4 different profiles for the first two sampling periods) to more than 9 different profiles detected in the June sampling with 8 other isolates having unique profiles. The June sampling appears to represent a major increase in the genetic diversity of the ruminal propionibacteria that was not evident in either of the first two sampling times.

In Vitro Ruminal Models for Selection:

Rumen fluid was collected from two cannulated dairy cows 2 hours post feeding. The rumen fluid was strained through 4 layers of cheese cloth into pre warmed (37° C.) thermos jugs. The rumen fluid was transported back to the lab where it was again strained through 4 layers of cheese cloth. A 100 ml of strained rumen fluid was added to individual pre warmed (37° C.) flasks containing 100 mls of sterile Merten's buffer (1 L $dH_2O$, 4.0 g ammonium bicarbonate, 35.0 g sodium bicarbonate). Strained rumen fluid solids (10 g) were added to each flask.

*Propionibacterium* strains to be used in the in vitro fermentations were grown in 10 ml tubes of sodium lactate broth (NLB) at 32° C. for 40 to 48 hours. For inoculation of the flasks, 2.0 ml of a 40 to 48 hour *Propionibacterium* culture was added to duplicate flasks containing the rumen fluid medium. The flasks were placed in a shaking water bath (37° C.). The mouth of each flask was sealed with a rubber stopper. The rubber stopper had 3 glass ports. Of the three ports, one port was connected (via rubber hosing) to a $CO_2$ tank to flush the flasks, one port served as an exhaust to vent the $CO_2$ flush, and a third port was used to remove samples for pH, VFA, and microbial analysis.

At hours 0, 6, 12, 24, 30, 36, 42, and 48 post inoculation, samples were removed from the flask through the sample ports for pH and volatile fatty acids analysis (VFA). The fluid collected for VFA analysis was placed into a microcentrifuge tube and centrifuged for 5 minutes at 10,000 rpm. A 0.5 ml sample of the centrifuged liquid was acidified with 0.5 ml of 10 mmol sulfuric acid. The acidified rumen fluid was filtered through a 0.2 um membrane filter (Gelman Laboratory Supor®-200). Volatile fatty acids were determined using a Bio Rad HPLC system. A 20 ul sample was injected into an HPX 87H column using a 5 mmol sulfuric acid mobile phase. One ml/minute flow rate.

Analysis of the VFA from in vitro rumen fluid fermentation flasks identified strains P169, P170, P179, P195 and P261 as the highest propionate producing strains. All strains identified were from genotype group 1. The presence of the 7.0 or 2.7 kb plasmid did not effect propionate production since strains that did not contain these plasmids produced similar levels of propionate. Strains P169, P170, P195, and P261 produced at least 0.9% (vol/vol) propionate in sodium lactate broth (NLB) and at least 0.2% (vol/vol) propionate in rumen fluid (in vitro). Strain P169 was used in subsequent animal trials described below.

Example 2

First Study of Isolates in Ruminants

Six non-lactating Holstein×Friesian dairy cows were fed a standard high forage diet (hay and grain, with a forage:grain ratio of 78/22). Cows had constant access to forage, and the grain was offered in two feeds per day at 8 a.m. and 5 p.m.

Two successive periods of testing were used. In period 1, which was weeks 1, 2, and 3, the cows were fed a control diet without *P. acidipropionici* strain P169. In period 2, which was weeks 4, 5, and 6, the cows were fed a control diet and the *P. acidipropionici* strain P169 was introduced directly into the rumen under the fiber layer.

Throughout the six week experimental period, measurements were taken of all food offered and all refusals. Cows were weighed at the start and end of each period. A pH measurement of the rumen fluid was taken.

At 08.00 h and 14.00 h, there was no effect of treatment (supplementation with *Propionibacterium*) on the rumen pH measured. However, in samples obtained at 19.30 h, cows that received the *Propionibacterium* had a significantly higher (P<0.01) rumen pH when compared with cows that had not received the *Propionibacterium*. The results indicate that, whereas in the control group, there was a decline in rumen pH during the 11.5 h after the morning allocation of concentrate (−0.486 pH units), in the cows which received the *Propionibacterium*, the decline in rumen pH occurred during 6 h after the morning feed (−0.32 pH units) and then remained relatively stable before returning to the prefeeding value.

While applicants do not wish to be restricted to a particular theory of the cause of the pH changes observed in the 3 animals, the following theory is one possible explanation. Lactate, which is a byproduct of ruminal digestion, was used by the Propionibacteria. Thus, the *Propionibacterium* had a physiological effect on the cows. Propionibacteria use lactate to form propionate and acetate, which are weaker acids than lactate. It is expected that if the rumen were tested at a later time, then it would show an increase propionate level.

Example 3

Second Study of Isolates in Ruminants

Nineteen pluriparous cows were assigned randomly to one of two dietary groups: total mixed ration (TMR) without Propionibacteria (control, n=10) or TMR plus Propionibacteria (Treated, n=9) from −2 wk to 12 wk postpartum. The cows were allowed free access to feed and water. Each treated cow received 17 g of a 1:10 preparation of the freeze-dried propionibacteria culture (strain P169 at $3.5 \times 10^{10}$ CFU/g) and maltodextrin carrier (strain P169) daily top-dressed into 1 to 2 kg of the TMR. Cows were individually fed and housed in a stanchion barn and grouped by treatment to prevent potential transfer of Propionibacteria from treated to control cows. Half of each group of cows was placed across each other and two unoccupied stalls with a plywood partition separated each adjacent group of cows. Each day cows were placed in a dry lot for two 5 to 6 h intervals (800 to 1300 and 2100 to 3000). One Propionibacteria-treated cow was taken out of the study due to a foot problem leaving nine cows in the treated group. Weekly BW were recorded and body condition of the cows were evaluated on wk 4 and 10 postpartum using a five point scale 1=very thin to 5=excessively fat.

The TMR was composed of sorghum silage, alfalfa hay, sorghum\sudan silage, whole cottonseed, and concentrate. Energy concentration of the diet was formulated to support daily milk production of 50 kg (NRC, 1989). Daily feed intake was recorded and the diet was sampled weekly and composited monthly for analysis.

Cows were milked twice daily (0300 and 1500 h), and milk yield was recorded. Milk samples were collected weekly during successive a.m. and p.m. milkings and analyzed for percent milk fat, protein, lactose, solids-non-fat (SNF), somatic cell count (SCC) and milk urea nitrogen (MUN). Milk production was corrected for percent milk fat (fat corrected milk (FCM)).

Blood samples (10 ml) were collected twice weekly via coccygeal venipuncture. After collection in tubes containing EDTA, blood was centrifuged at 1200×g for 20 min (5° C.), and plasma was decanted and stored frozen at −20° C. for subsequent analysis.

Figure 3:
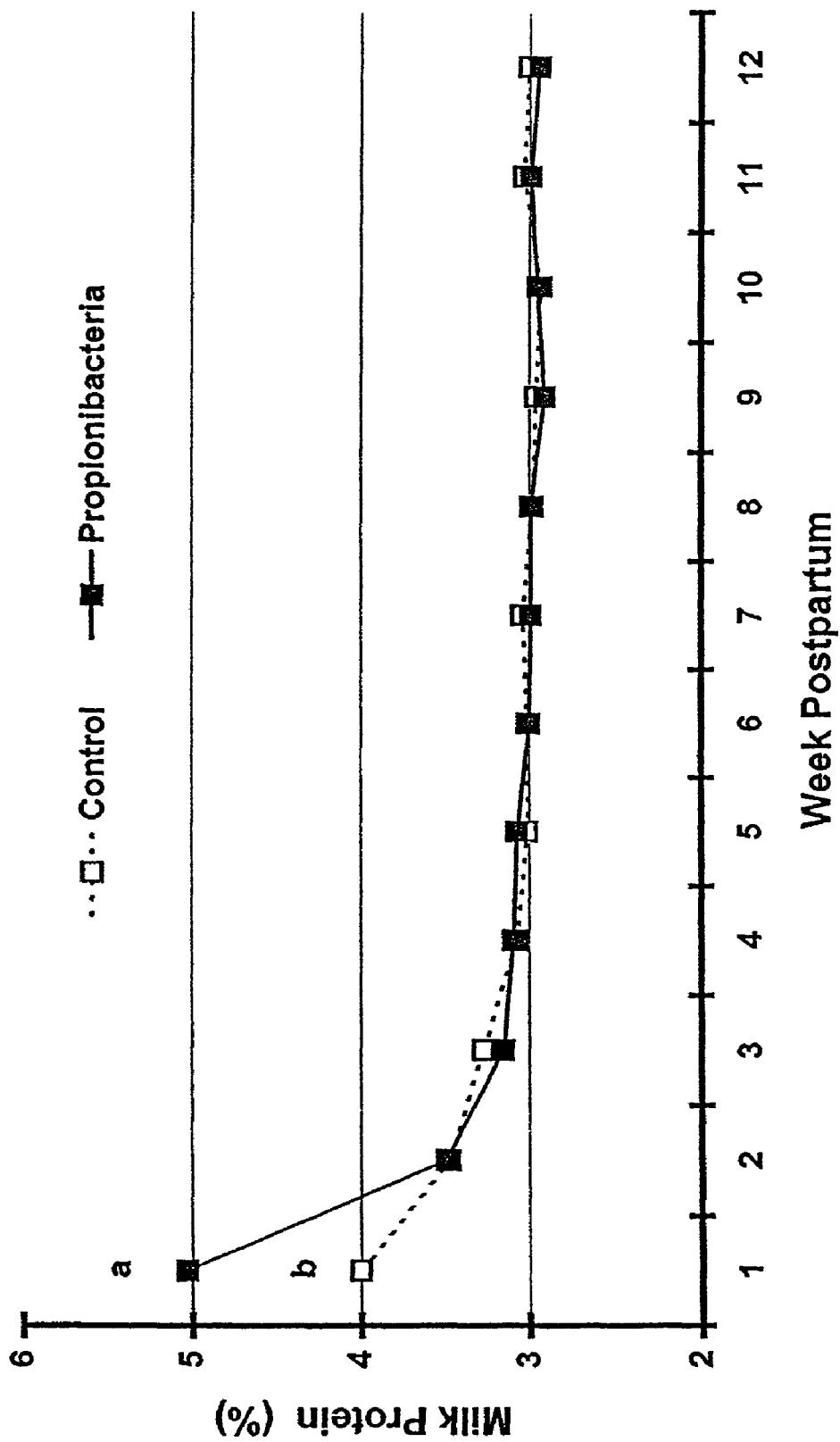
FIG. 3 shows weekly changes in percent milk protein of postpartum cows fed Propionibacteria (n=9) and control (n=10) diets during the first 12 wk of lactation. Means with different superscript within week differ (P<0.01). SEM=0.14 for control and 0.15 for treatment cows.

Milk Protein: There was a significant interaction (P<0.001) between treatment and week postpartum on percent milk protein. Propionibacteria-treated cows had higher (P<0.001) percent milk protein on wk 1 of lactation than control cows but not in the subsequent weeks (FIG. 3). Percent milk protein decreased from wk 1 to 3 and plateaued from wk 4 to 12 in both groups of cows (FIG. 3).

Figure 4:
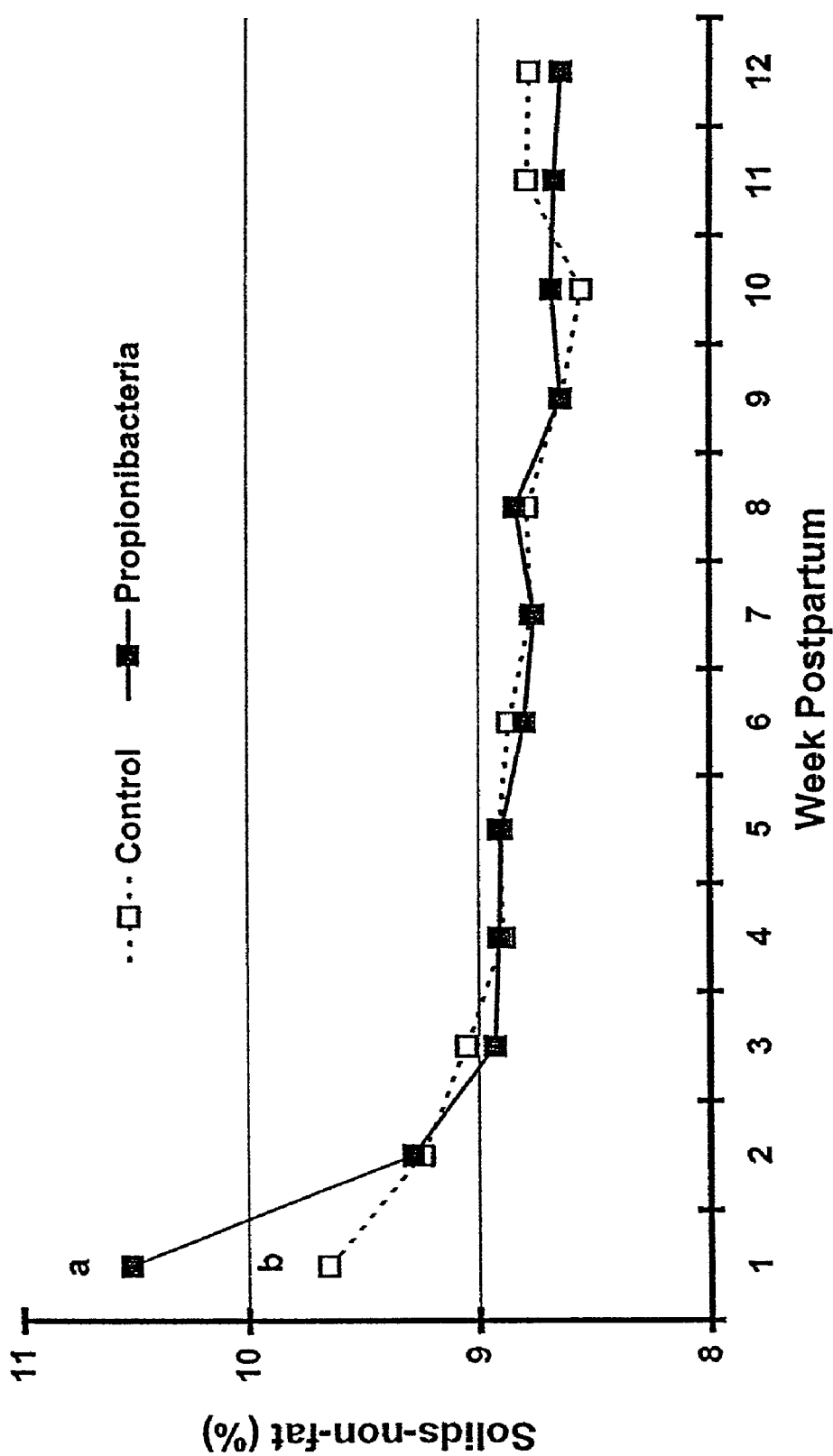
FIG. 4 illustrates weekly changes of percent solids-non-fat of postpartum cows fed Propionibacteria (n=9) and control (n=10) diets during the first 12 wk of lactation. Means with different superscript within week differ (P<0.05). SEM=0.14 for control and 0.15 for treatment cows.

Solids-Non-Fat: There was a significant interaction between treatment and week postpartum (P<0.05) on percent milk SNF. Propionibacteria-treated cows had higher (P<0.001) percent SNF on wk 1 of lactation than control cows but not during the following weeks (FIG. 4). Percent SNF decreased from wk 1 to 3 and remained stable in the subsequent weeks in both groups of cows (FIG. 4).

Figure 5:
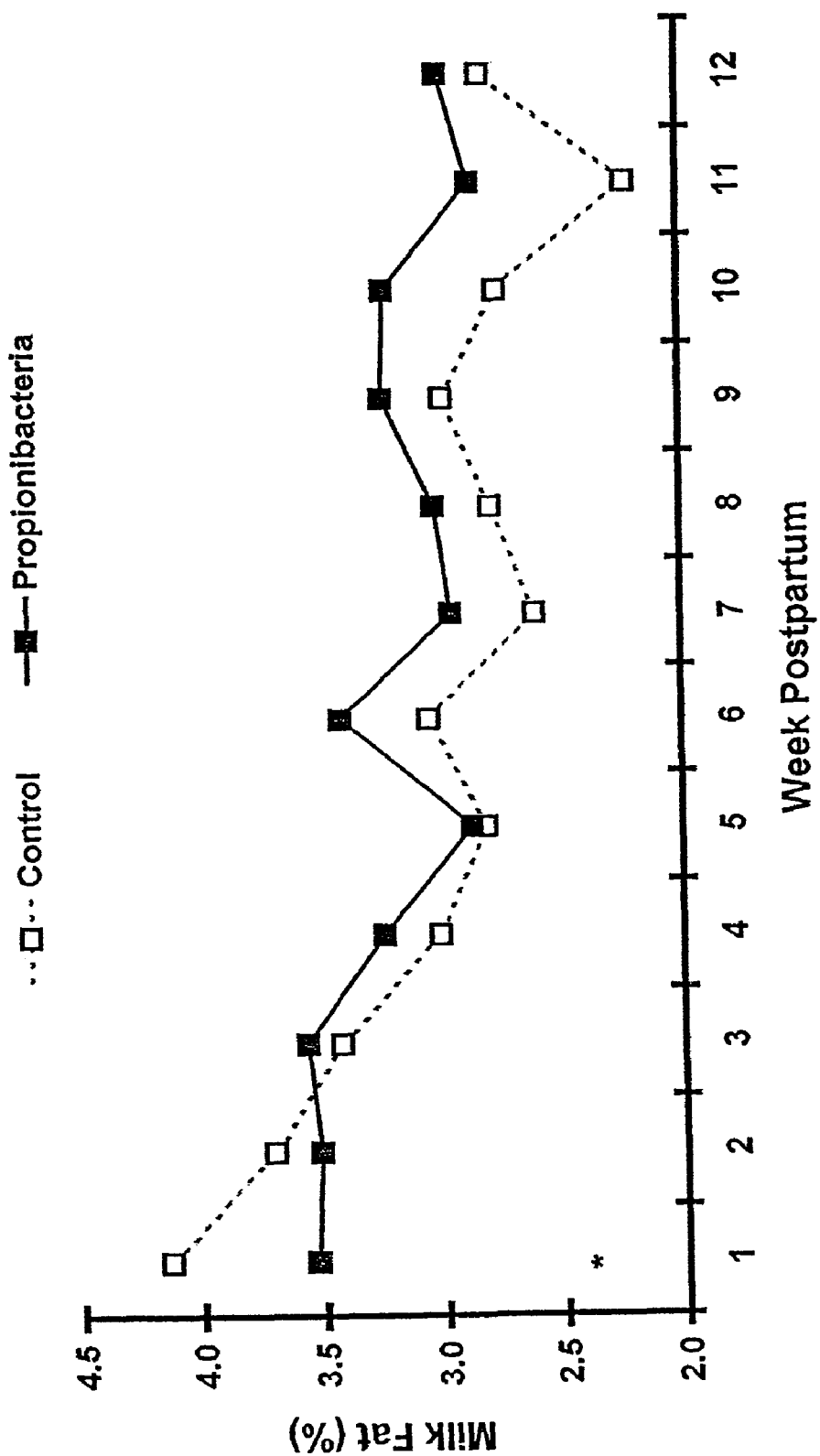
FIG. 5 displays weekly changes in percent milk fat of postpartum cows. Data from cows fed (see attached for new figure.) Propionibacteria (n=9) and control (n=10) diets during the first 12 wk postpartum. SEM was 0.08 for control and 0.08 for treatment cows. *Means within week differ (P<0.13).

Milk Fat: There was a significant interaction between treatment and week postpartum on percent milk fat The average milk fat percentage tended to differ (P=0.13) between Propionibacteria-treated (3.2±0.08%) and control (3.02±0.08%) cows. (FIG. 5).

Figure 6:
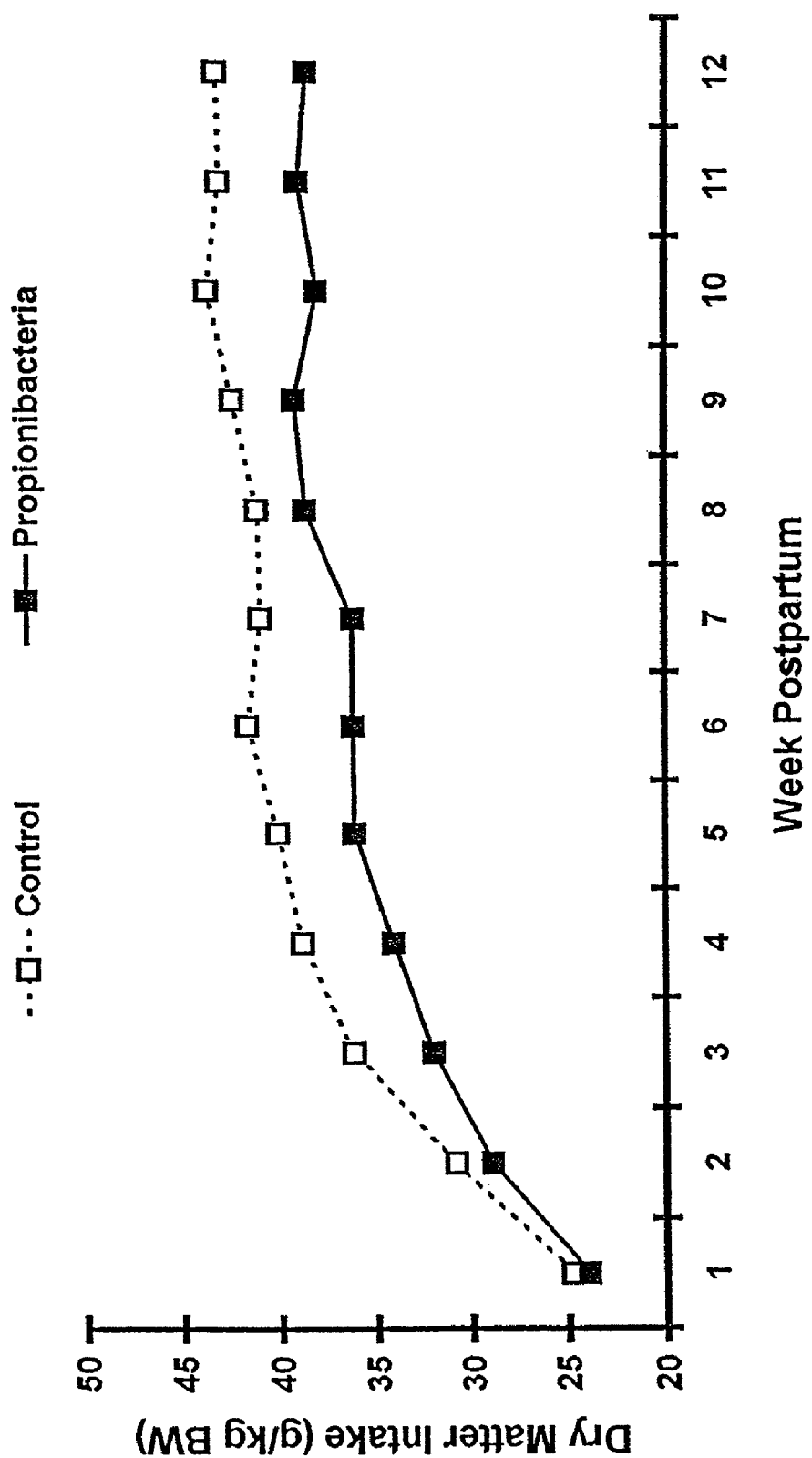
FIG. 6 displays weekly changes in dry matter intake (DMI) expressed as g dry matter per kg of body weight (BW) of postpartum cows Propionibacteria (n=9) and control (n=10) diets during the first 12 wk postpartum. SEM was 0.8 for control and 0.8 for treatment cows. *Means within week differ (P<0.01).

Dry Matter Intake: DMI expressed as g DMI per kg body weight (BW) differed significantly (P<0.01) between Propionibacteria-treated and control cows. Averaged over the 12-wk period, control and Propionibacteria-treated cows consumed 23.97±0.48 and 23.37±0.50 kg/d, respectively. However, treated cows weighed more (667.1 kg±19 kg) than control cows (616.2±18 kg) and when expressed on a body weight basis was significantly different (FIG. 6).

Figure 7:
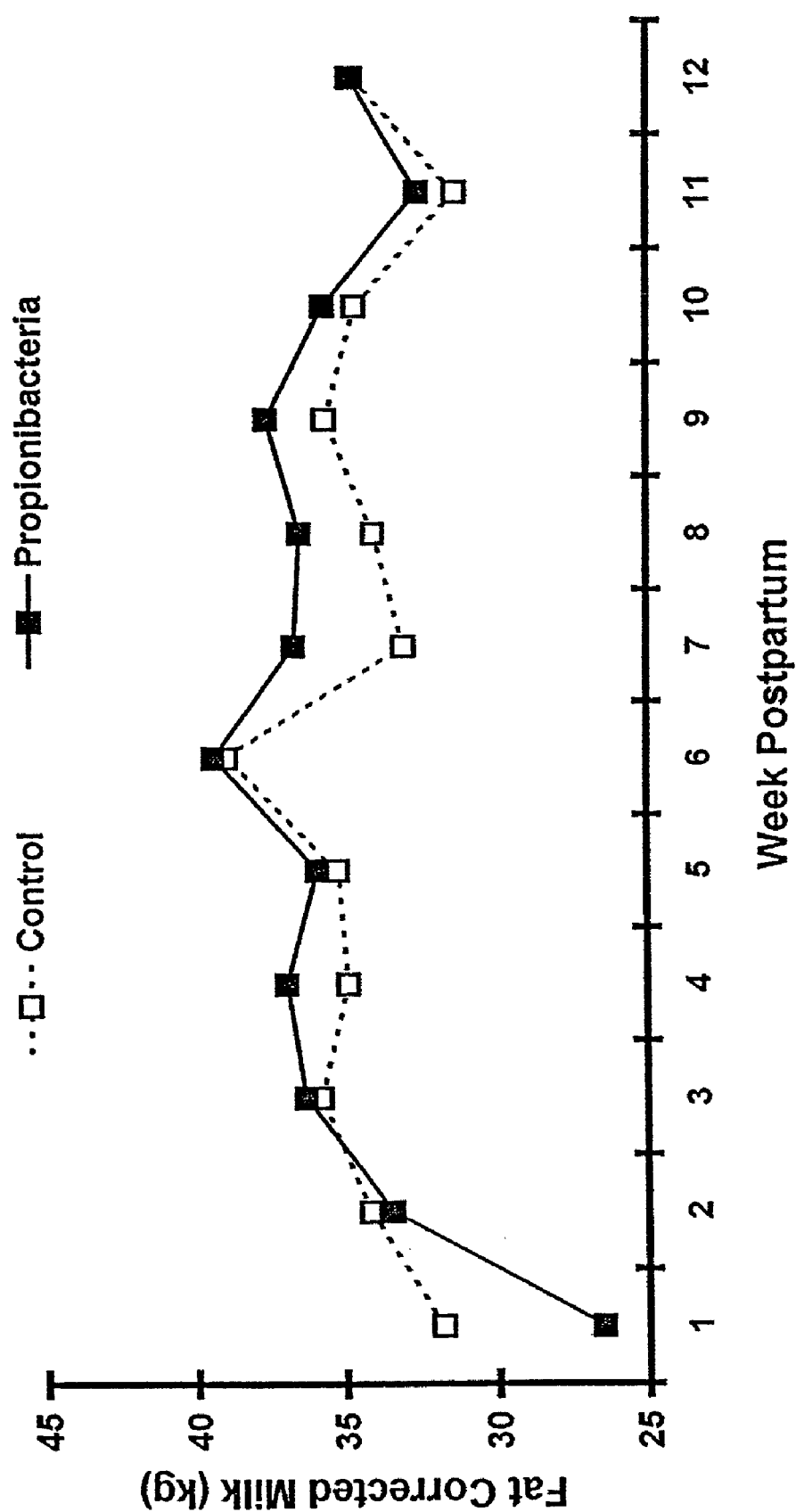
FIG. 7 shows weekly changes in fat correct milk of postpartum cows fed Propionibacteria (n=9) and control (n=10) diets during the first 12 wk postpartum. There was no significant effect of treatment over the 12 wk (P>0.7).

Fat Corrected Milk: The interaction of treatment and week postpartum did not affect (P>0.50) FCM. FCM production did not differ between the control and treated cows over the 12-wk study. Control and Propionibacteria-treated cows produced 34.49 t 0.86 and 35.16±0.89 kg/d, respectively. (FIG. 7) The FCM results show that cows did not decrease in production when they consumed less.

Glucose and Insulin: Plasma concentrations of insulin were determined by using solid-phase insulin RIA kit (Micromedic Insulin Kit, ICN Biomedicals, Costa Mesa, Calif.) except that bovine insulin was used as a reference standard (25.7 IU/mg) as previously described (Simpson et al., 1994). Intraassay and interassay coefficients of variation were 12.8% and 7.8%, respectively.

Plasma concentrations of glucose were determined using Glucose kits (Roche Diagnostic Systems, Inc., NJ) and a clinical analyzer (Cobas FARA II, Roche Analytical Instrument, Montclaire, N.J.). This procedure was based on the hexokinase coupled with glucose-6-phosphate dehydrogenase enzymatic reaction. The intraassay coefficient of variation was 2.3%.

Neither plasma glucose (P>0.10) nor plasma insulin (P>0.50) concentrations were affected by the interaction of treatment×week postpartum. Cows fed Propionibacteria had an average plasma glucose concentration 60.00±0.91 mg/dl comparable (P>0.50) to that of control cows 60.02±0.88 mg/dl. Concentrations of glucose in plasma increased (P<0.01) with wk postpartum such that wk 2 average glucose concentration was higher by 24% (P<0.02) than wk 1. Plasma glucose level did not change significantly after wk 2 postpartum, indicating that reproductive function was maintained.

Average plasma concentration of insulin in cows fed Propionibacteria was similar (P>0.10) to the control cows (0.39±0.02 vs. 0.42±0.02 ng/ml). Concentrations of insulin in plasma increased (P<0.001) with week postpartum such that insulin concentrations at wk 2 differed from wk 1 (P<0.10). Plasma insulin concentrations increased gradually thereafter such that over the 12-wk period, plasma insulin increased twofold (0.25±0.03 ng/ml in wk 1 to 0.51±0.03 ng/ml in wk 12), indicating that reproductive function was maintained.

Non-Esterified Fatty Acids and Leptin: NEFA concentrations were determined by enzymatic method using NEFA-C kits (Waco Chemicals USA, Inc., VA) and a clinical analyzer (Cobas FARA II, Roche Analytical Instrument, Montclaire, N.J.). This enzymatic method utilizes acyl-CoA synthethase and acyl-CoA oxidase to produce 3-methyl-N-ethyl-N-(B-hydroxyethyl)aniline (MEHA). The intraassay coefficient of variation was 4.5%.

Leptin plasma concentrations were measured using a Multi-species RIA kit assay (LINCO Research, Inc., St. Charles, Mo.) according to the manufacturer's recommendations with minor modifications. Briefly, on the first day, 100 Al of first antibody were added to all tubes except total count (TC) and non-specific binding (NSB) tubes then vortexed, covered and incubated for 24 h at 4° C. The standard curve was modified to include 1, 2, 3, 5, 10 and 20 ng/ml of human leptin standard. On the second day, 100 pl of the tracer (1 251-human leptin) was added to all tubes then incubated for another 24 h at 4° C. On the third day, 1.0 ml of precipitating reagent was added to all tubes except TC tubes then incubated for 20 min at 4° C. Tubes were centrifuged at 3,000×g for 30 min, then supernatant was decanted and precipitate was counted using the Gamma Counter. The sensitivity of the assay as defined as 95% of total binding was 0.85±0.08 ng/ml.

Figure 8:
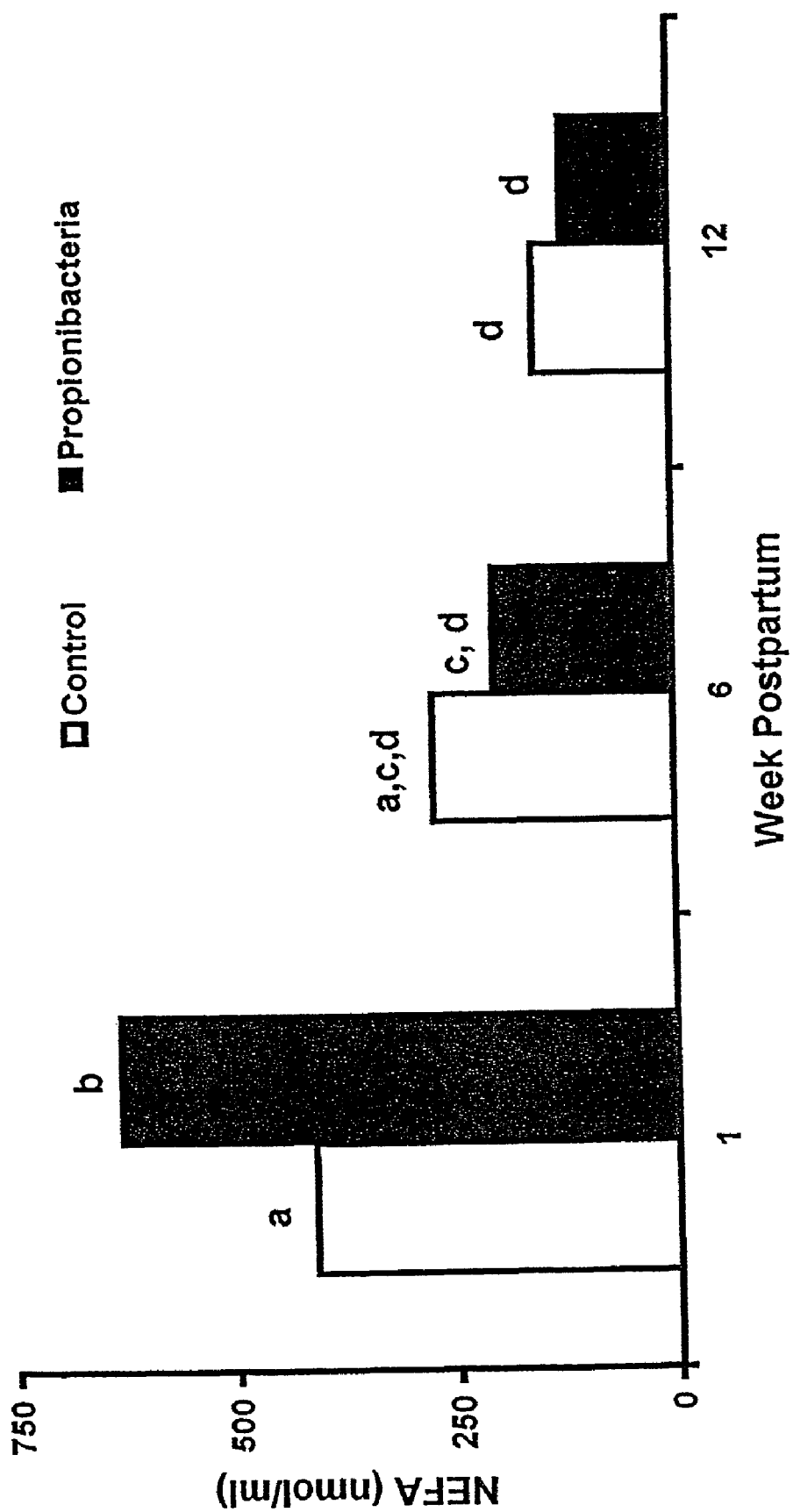
FIG. 8 shows changes in plasma non-esterified fatty acids (NEFA) concentrations of postpartum cows during the first 12 wk of lactation. Data from cows fed Propionibacteria (n=9) and control (n=10) diets. Means without a common superscript differ (P<0.01). SEM=47 for control and 49 for treatment cows.
Figure 9:
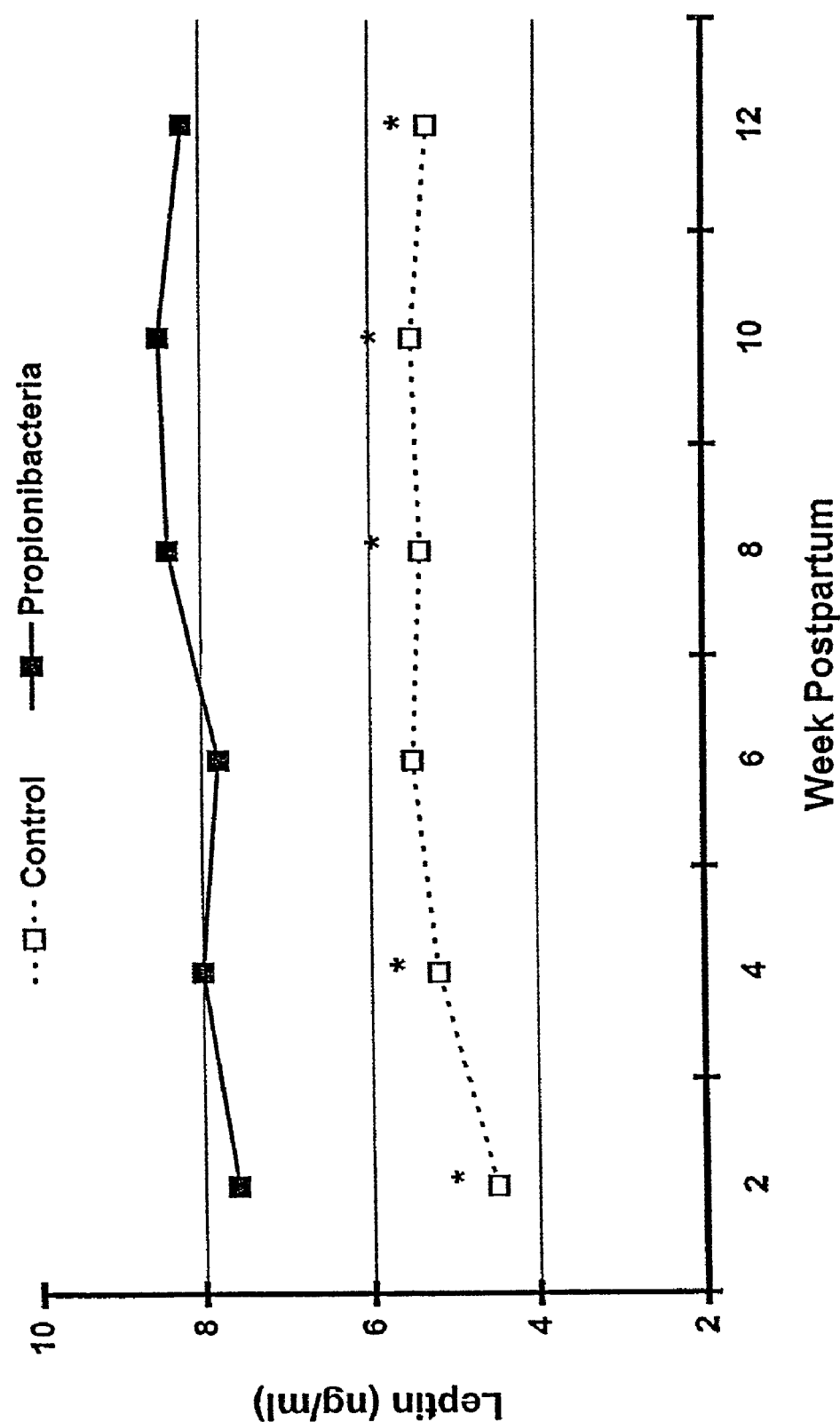
FIG. 9 illustrates weekly changes in plasma leptin concentrations of postpartum cows fed Propionibacteria (n=9) and control (n=10) diets during the first 12 wk of lactation. *Mean within week differs (P<0.10) from Propionibacteria mean. Pooled SEM=1.1 for control and 1.1 for Propionibacteria treated cows.

There was a significant (P<0.01) treatment×week postpartum interaction on plasma NEFA concentrations. Plasma NEFA concentrations of Propionibacteria-treated cows at wk 1 postpartum were greater (P<0.01) than control cows (FIG. 9). Plasma NEFA concentrations decreased (P<0.001) with week postpartum for both groups of cows, although the decrease was more dramatic in Propionibacteria-treated than control cows (FIG. 8), indicating that cows that were fed Propionibacteria were moving towards positive energy balance.

Plasma leptin concentrations were significantly different (P<0.10) in Propionibacteria-treated cows (8.10±1.0 ng/ml) compared to control cows (5.25±1.0 ng/ml) (FIG. 9), demonstrating that the direct fed Propionibacteria had a positive effect on cows' plasma leptin, which may be an important signal for regulation of feed consumption that indirectly affects milk production, energy status, and reproductive functions. Treatment×week interaction (P>0.50) and week postpartum (P>0.50) did not affect plasma leptin concentrations (FIG. 9).

EB Calculations: EB was calculated by using net energy intake as the average daily DMI multiplied by the net energy concentration of the diet. Net energy required for daily maintenance of the animals was derived using the equation 80×BW '75 (kg)/1000 (NRC, 1989). Daily energy for milk production was calculated using the formula (Tyrell and Reid, 1965), Milk yield (kg)×[92.239857 (% milk fat)+49.140211 (% SNF)−56.393297]/1000 where milk yield is average daily yield for the week, and milk composition based on weekly milk analysis. This equation reflects the metabolic status of the cow more accurately than the conventional method of measuring milk yield alone (Butler and Smith, 1989).

Figure 10:
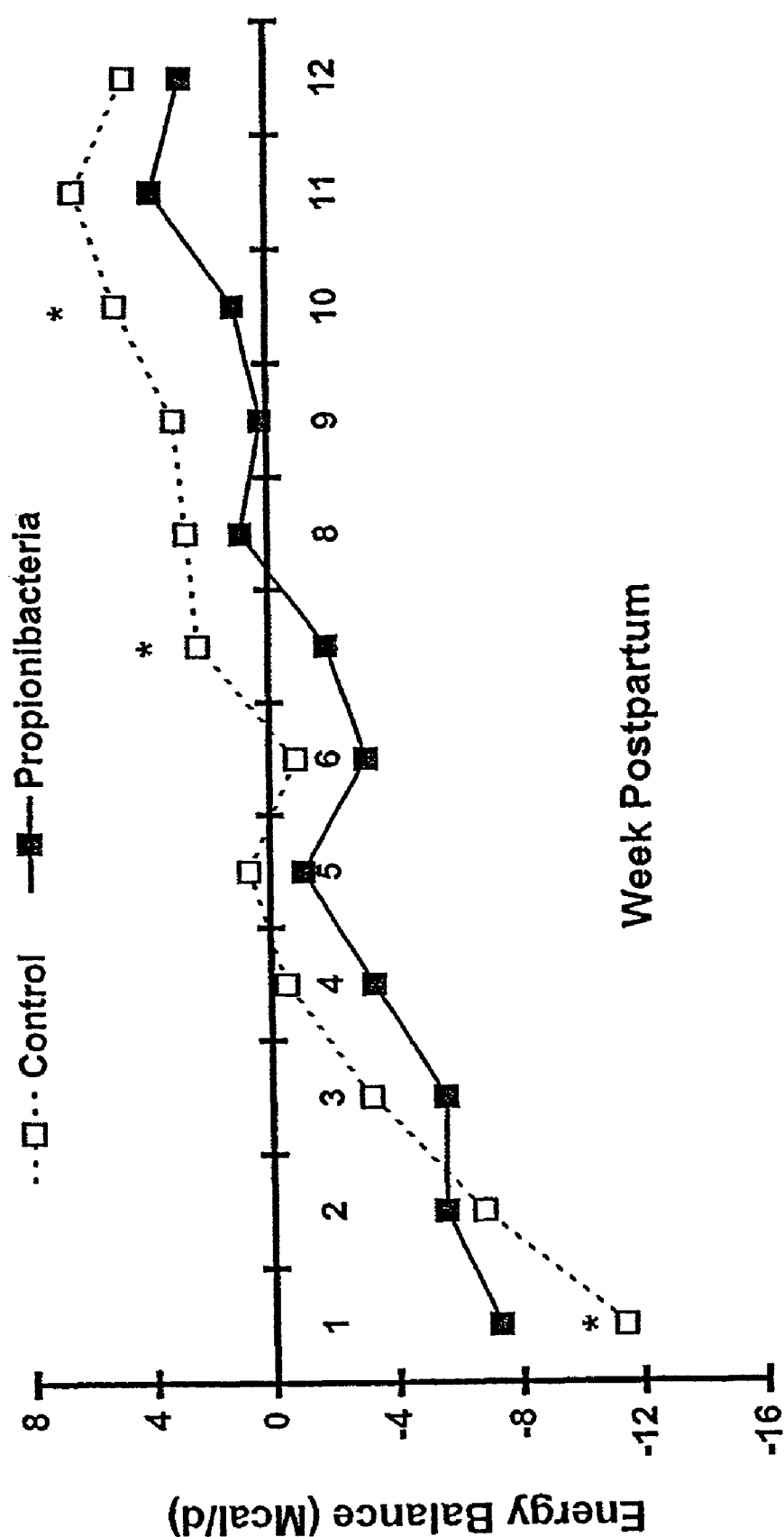
FIG. 10 demonstrates weekly changes in energy balance of postpartum cows fed Propionibacteria (n=9) and control (n=10) diets during the first 12 wk postpartum. SEM was 1.48 for control and 1.54 for treatment cows. *Means within week differ (P<0.10).

EB was not influenced (P>0.10) by interaction of treatment×week postpartum, but EB was affected (P<0.001) by week postpartum and treatment (P<0.10) (FIG. 10). Generally, both groups of cows gained a positive EB starting 8 wk of lactation. Specifically, postpartum weeks 1, 3 and 6 differed (P<0.05) from their succeeding week by −3.1, −2.5, and −2.27 Mcal/d, respectively (FIG. 10). Average EB of postpartum cows tended to differ (P<0.10) between cows fed with Propionibacteria (−1.596±0.72 Mcal/d) and control cows (0.196±0.69 Mcal/d) during the 12-wk feeding period.

The interaction of treatment×week postpartum did not affect (P>0.50) body weight (BW). During the first 12 wk of lactation, average BW of postpartum cows tended to differ (P<0.10) between Propionibacteria-treated (667.1 kg±19 kg) and control (616.2±18 kg) cows. Also, weekly BW differed (P<0.001) among weeks postpartum. In both groups of cows, BW decreased between wk 1 and wk 3 but did not significantly change between wk 5 and wk 12 of lactation (data not shown).

The interaction (P>0.50) between treatment×week postpartum did not affect average body condition score (BCS). Also, treatment had no affect (P>0.50) on BCS, measured at wk 4 and 10 postpartum. The BCS ranged from was 2.5 to 3.75 and averaged 2.69± for control cows and 2.68±0.06 for Propionibacteria-treated cows. Average weekly BCS increased significantly (P<0.01) from wk 4 to wk 10 (2.53±0.07 vs. 2.86±0.06) in both groups of cows.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention. For example, the invention is applicable to other lactating ruminants, such as sheep and goats.

The invention is not intended to be limited to the preferred embodiments described above, but rather is intended to be limited only by the claims set out below. Thus, the invention encompasses all alternate embodiments that fall literally or equivalently within the scope of these claims.

BIBLIOGRAPHY

Amaral-Phillips, D. M., A. D. McGilliard, G. L. Lindberg, J. J. Veenhuizen, J. J., and J. W. Young. 1993. Effects of decreased availability of glucose for dairy cows. J. Dairy Sci. 76:752-761.

Beam, S. W. and W. R. Butler. 1998. Energy Balance, metabolic hormones, and early postpartum follicular development in dairy cows fed prilled lipid. J. Dairy Sci. 81:121-131.

Berghorn, K. A., R. D. Allrich and C. H. Noller. 1988. Influence of energy balance on postpartum reproduction. Page 65 in Purdue Dairy Day Rep., Purdue Univ., West Lafayette, Ind.

Canfield, R. W. and W. R. Butler. 1991. Energy balance, first ovulation and the effects of naloxone on LH secretion in early postpartum dairy cattle. J. Anim. Sci. 69: 740746.

Carrol, D. J., M. J. Jerred, R. R. Grummer, D. K. Combs, R. A. Pierson, and E. R. Hauser. 1990. Effect of fat supplementation and immature alfalfa to concentrate ratio on plasma progesterone, energy balance, and reproductive traits of cattle. J. Dairy Sci 73:2855-2863.

Gong, J. G., D. McBride, T. A. Bramley, and R. Webb. 1994. Effects of recombinant bovine somatotropin, insulin-like growth factor I and insulin on bovine granulosa cell steroidogenesis in vitro. J. Anim. Sci. 143:157-164.

Grummer, R. R. and D. J. Carroll. 1991. Effects of dietary fat on metabolic disorders and reproductive performance of dairy cattle. J. Anim. Sci. 69: 3838-3852. Grummer, R. R. and D. J. Carroll. 1988. A review of lipoprotein cholesterol metabolism: importance to ovarian function. J. Anim. Sci. 66:3160-3173.

Hawkins, G. E., K. A. Cummins, M. Silverio and J. J. Jilek. 1985. Physiological effects of whole cottonseed in the diet of lactating dairy cows. J. Dairy Sci 0.68:2608-2614.

Huhtanen, P., H. Miettinen, and M. Ylinen. 1993. Effect of increasing ruminal butyrate on milk yield and blood constituents in dairy cows fed a grass silage-based diet. J. Dairy Sci. 76:1114-1124.

Jonsson, N. N., R. C. Daniel, D. Mayer and R. Verrall. 1998. Effects of oral dosing with calcium propionate on total calcium and glucose concentrations in the plasma of the cow. Zentralbl Verinarmed A 45:127-136.

Kimura, M., Nakao, T., Moriyoshi, M. and Kwata, K. 1987. Luteal phase deficiency as a possible cause of repeat breeding in dairy cows. Brit. Vet. J. 143:560-566.

Koprowski, J. A. and H. A. Tucker. 1973. Bovine serum growth hormone, corticoids and insulin during lactation. Endocrinology 93:645-651.

Kronfeld, D. S., S. Donoghue, J. M. Naylor, K. Johnson and C. A. Bradley. 1980. Metabolic effects of feeding protected tallow to dairy cows. J. Dairy Sci. 63:545552. Littell, R. C., Milliken, G. A., Stroup, W. W., and Wolfinger, R. D. 1996. SAS System for Mixed Models. SAS Inst. Inc., Cary, N.C.

McArdle, C. A., Kohl, C., Rieger, K., and Wehrenberg, U. 1991. Effects of gonadotropins, insulin, and insulin like growth factor I on ovarian oxytocin and progesterone production. Mol Cell Endocrinol. 78:211-220.

McArdle, C. A. and Holtorf, A. P. 1989. Oxytocin and progesterone release from bovine corpus luteal cells in culture: Effects of insulin-like growth factor I, insulin and prostaglandins. Endorinology 124:1278-1286.

McDonald, E, R. A. Edwards, J. F. D. Greenhalgh and C. A. Morgan. 1987. Animal Nutrition. (5th ed). Singapore: Longman Singapore Pub. (Pte) Ltd. p. 202.

Oshio, S., I. Tahata and H. Minato. 1987. Effects of diets differing in rations of roughage to concentrate on microflora in the rumen of heifers. J. Gen. Appl. Microbiol. 33:99.

Ronge, H., Blum, J. Clement, C., Jans, F., Leuenberger, H., and Binder, H. 1988. Somatomedin C in dairy cows related to energy and protein supply and to milk production. Anim. Prod. 47:165-183.

Saumande, J. 1991. Culture of bovine granulosa cells in a chemically defined serum-free medium: The effect of insulin and fibronectin on the response to FSH. J. Steroid Biochem. Mol. Biol. 38:189-196.

Schams, D., Koll, R., and Li, C. H. 1988. Insulin-like growth factor I stimulates oxytocin and progesterone production by bovine granulosa cells in culture. J. Endocrinol 116:97-100.

Sklan, D., U. Moallem and Y. Folman. 1991. Effect of feeding calcium soaps of fatty acids on production and reproductive responses in high producing lactating cows. J. Dairy Sci. 74:510-517.

Smith, et al. 1978. Effects of feeding protected tallow to dairy cows in early lactation. J. Dairy Sci. 61:747-756. Spicer, L. J., A. Alpizar, and S. E. Ecternkamp. 1993. Effects of insulin, insulin-like growth factor 1, and gonadotropins on bovine granulosa cell proliferation, progesterone production, estradiol production, and (or) insulin-like growth factor I production in vitro. J. Anim. Sci. 71:1232-1241.

Spicer, L. J. and C. S. Chamberlain. 1998. Influence of cortisol on insulin- and insulinlike growth factor 1 (IGF-1)- induced steroid production and on IGF-1 receptors in cultured bovine granulosa cells and thecal cells. Endocrine 9:153-161.

Spicer, L. J., W. B. Tucker. and G. D. Adams. 1990. Insulin-like growth factor-I in dairy cows: Relationships among energy balance, body condition score, ovarian activity, and estrous behavior. J. Dairy Sci. 73:929-937.

Spicer, L. J., R. K. Vernon, W. B. Tucker, R. P. Wettemann, J. F. Hogue, and G. D. Adams 1993. Effects of inert fat on energy balance, plasma concentrations of hormones and reproduction in dairy cows. J. Dairy Sci. 76:2664-2673.

Staples, C. R. and W. W. Thatcher. 1990. Relationship between ovarian activity and energy status during the early postpartum period of high producing dairy cows. J. Dairy Sci. 73:938-947.

Talayera, F., C. S. Park and G. L. Williams. 1985. Relationships among dietary lipid intake, serum cholesterol and ovarian function in Holstein heifers. J. Anim. Sci. 60:1045-1051.

Villa-Godoy, A., T. L. Hughes, R. S. Emery, L. T. Chapin and R. L. Fogwell. 1988. Association between energy balance and luteal function in lactating cows. J. Dairy Sci. 71:1063-1072.

What is claimed is:

1. A method of feeding a ruminant, the method comprising: feeding an effective amount to colonize the rumen of the ruminant the *Propionibacterium acidipropionici* strain P169 ATCC PTA-5271 to the ruminant; and
after the feeding, testing the ruminant for a least one of energy balance, plasma non-esterified fatty acids levels, glucose levels, propionate levels, and plasma leptin levels,
wherein the feeding of the strain increases at least one of energy balance, plasma non-esterified fatty acids levels, glucose levels, propionate levels, and plasma leptin levels in the first ruminant when compared to the respective energy balance, plasma non-esterified fatty acids levels, glucose levels, propionate levels, and plasma leptin levels in an untreated control ruminant not fed the strain.

2. The method of claim 1, wherein the energy balance is increased.

3. The method of claim 1, wherein the plasma non-esterified fatty acids levels are increased.

4. The method of claim 1, wherein the plasma leptin levels are increased.

5. The method of claim 1, wherein the glucose levels are increased.

6. The method of claim 1, wherein the propionate levels are increased.

7. The method of claim 1, wherein the ruminant is a bovine.

8. The method of claim 1, wherein the ruminant is fed the strain at a level such that the ruminant is dosed daily with about $6 \times 10^9$ CFU to about $6 \times 10^{12}$ CFU/animal/day.

9. The method of claim 8, wherein the ruminant is fed the strain at a level such that the ruminant is dosed daily with about $6 \times 10^{11}$ CFU/animal/day.

10. The method of claim 1, wherein the ruminant is fed the strain until populations of $10^5$ to $10^8$ CFU/ml ruminal fluid are established in the rumen of the first ruminant.

11. The method of claim 1, wherein the ruminant is fed the strain from −2 to 12 weeks postpartum.

* * * * *